United States Patent [19]

Miyamoto et al.

[11] Patent Number: 5,461,170

[45] Date of Patent: Oct. 24, 1995

[54] PROCESS FOR PREPARATION OF POLYOL FATTY ACID ESTER AND GLYCERIDE MIXTURE OBTAINED

[75] Inventors: Ayari Miyamoto, Chiba; Akira Shigeta, Tokyo; Yukitaka Tanaka, Ibaraki; Hisao Oomura, Ibaraki; Kenji Masui, Ibaraki; Masahiro Katada, Ibaraki; Masahiko Asahi, Tokyo; Takashi Komori; Toshiyuki Suzuki, both of Chiba, all of Japan

[73] Assignee: Kao Corporation, Tokyo, Japan

[21] Appl. No.: 977,894

[22] Filed: Nov. 18, 1992

Related U.S. Application Data

[62] Division of Ser. No. 771,517, Oct. 3, 1991, abandoned, which is a continuation of Ser. No. 246,875, Sep. 29, 1988, abandoned.

[30] Foreign Application Priority Data

Oct. 14, 1987 [JP] Japan .................................. 62-259130
Oct. 20, 1987 [JP] Japan .................................. 62-264080
Oct. 30, 1987 [JP] Japan .................................. 62-275221

[51] Int. Cl.$^6$ .......................... C07C 59/235; C07C 59/00
[52] U.S. Cl. ............................................ 554/213; 554/227
[58] Field of Search ...................................... 554/213, 227

[56] References Cited

U.S. PATENT DOCUMENTS 4,416,991  11/1983  Matsuo et al. .......................... 435/134

*Primary Examiner*—José G. Dees
*Assistant Examiner*—Dwayne C. Jones
*Attorney, Agent, or Firm*—Flynn, Thiel, Boutell & Tanis

[57] ABSTRACT

A polyol fatty acid ester having mixed acid groups is produced by reacting a partial ester of a polyol and a branched fatty acid with a a straight chain fatty acid or a lower alcohol ester thereof in the presence of a lipase. The obtained glyceride mixture contains a large amount of diglyceride having a branched, saturated fatty acid group and a straight chain, saturated fatty acid group.

1 Claim, 1 Drawing Sheet

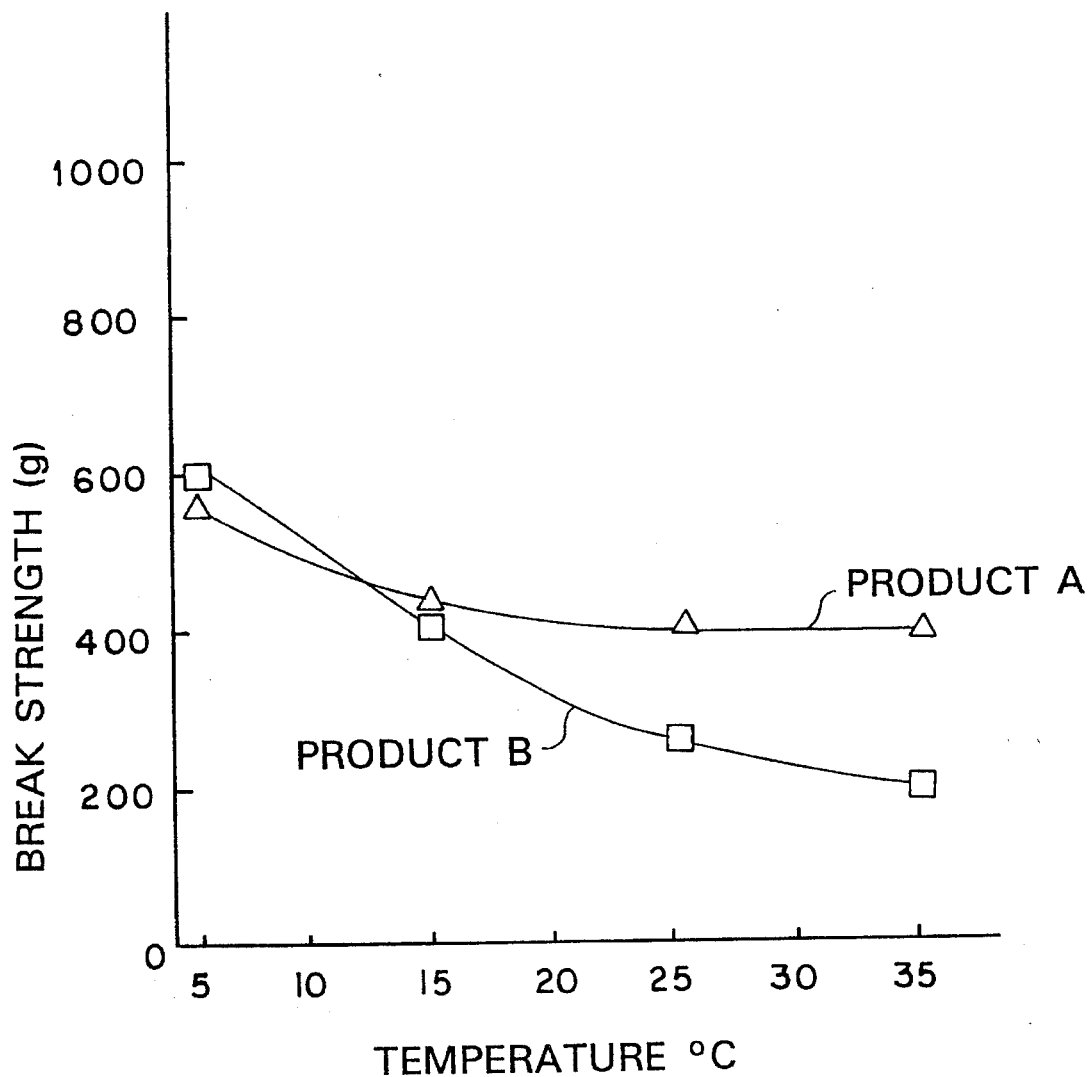

PROCESS FOR PREPARATION OF POLYOL FATTY ACID ESTER AND GLYCERIDE MIXTURE OBTAINED

This is a division of Ser. No. 07/771,517, filed Oct. 3, 1991, abandoned on Feb. 4, 1993 which is a continuation of U.S. Ser. No. 07/246,875, filed Sep. 20, 1988 abandoned on Oct. 3, 1991.

The present invention relates to a process for the preparation of polyol fatty acid esters. More particularly, the present invention relates to a process for preparing a polyol fatty acid ester having a mixed acid residue of a branched fatty acid and a straight-chain fatty acid in the molecule at a high purity and which is easily obtained according to the enzyme method. The invention also relates to a glyceride mixture obtained by the claimed process and a composition containing the glyceride mixture for external and cosmetic use.

STATEMENT OF PRIOR ARTS

As a process for the industrial production of fatty acid esters, which is commonly used, there can be mentioned an esterification process and an alcoholysis process. However, a process for preparing, at a high purity, a polyol fatty acid ester having a mixed acid residue of a branched fatty acid and a straight-chain fatty acid in the molecule, which is intended in the present invention, is not common.

In the case where a polyol is esterified with mixed fatty acids of a branched fatty acid and a straight-chain fatty acid, in the presence or absence of a catalyst, since the reactivity of the hydroxyl groups of the polyol are not selective, various polyol fatty acid esters having random ester linkages are synthesized.

For example, in the synthesis of a glycerol ester with a branched fatty acid (B) and a straight-chain fatty acid (S), if a triglyceride is intended, there is formed a mixture in which six triglycerides

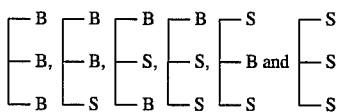

and are randomly distributed in the fatty acid composition, wherein

represents glycerol. If a diglyceride is intended, there are formed three diglycerides

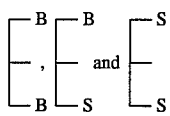

(neglecting the distinction between 1,2-diglyceride and 1,3-diglyceride) and the above-mentioned triglyceride mixture.

As a process for preparing a polyol ester having a mixed acid residue of a branched fatty acid and a straight-chain fatty acid (in the above-mentioned example,

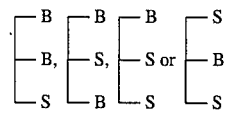

in the case of the triglyceride and

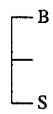

in the case of the diglyceride), there can be considered a process in which a mixture formed by esterification is subjected to the solvent fractionation and a fraction of the ester having a mixed acid residue is concentrated. However, if the difference in the melting point or solubility is small, the concentration thereof is substantially impossible, and even if a high concentration is obtained, the yield is very low and the process is not practical.

There can be considered another process in which a partial ester of a branched fatty acid or a straight-chain fatty acid is synthesized in advance by esterification and the partial ester is reacted with a halide or the like of the remaining fatty acid (a straight-chain fatty acid for the partial ester of the branched fatty acid or a branched fatty acid for the partial ester of the straight-chain fatty acid). Also in this process, however, since the remaining hydroxyl group of the partial ester has no selectivity, a product esterified selectively at a predetermined position cannot be efficiently obtained. Moreover, a product satisfactory in quality and safety can hardly be obtained.

A polyol ester inevitably having a mixed fatty acid residue of a branched fatty acid and a straight-chain fatty acid in the molecule has not been studied with a few exceptions (for example, Japanese Patent Publication No. 20362/1985), and an ester composition comprising such an ester at a high concentration has not been studied at all.

As the result of research made by us, it was found that these polyesters have several characteristics not possessed by conventional straight-chain fatty acid esters or branched fatty acid esters or mixtures thereof. For example, a branched/straight-chain mixed acid ester, which is in liquid form, has a characteristic viscosity and low-temperature resistance, and a branched/straight-chain mixed acid ester, which is in solid form, is prominently characterized by stretchability and crystallinity.

It is considered that the reason why a polyol ester having a mixed acid residue of a branched fatty acid and a straight-chain fatty acid, as mentioned above, has not attracted attention, is that a practical and-economical preparation process has not been established. However, even if good production methods of such a mixed acid ester are conceived, since the ester is contained as a part of a mixture, the effect is not sufficiently exerted.

As pointed out hereinbefore, according to the conventional chemical processes, such as esterification or alcoholysis processes, for the production of a polyol ester having a mixed acid residue of a branched fatty acid and a straight-chain fatty acid, the fatty acid distribution is random, and even if a concentrating means such as distillation or fractionation is adopted, increase in the purity of the intended polyol ester having a mixed acid residue is limited.

SUMMARY OF THE INVENTION

We made research with a view to solving the above-mentioned problem, and as the result, it was found that by using an enzyme (lipase) process, a polyol ester having a mixed acid residue of a branched fatty acid and a straight-chain fatty acid, which has a high purity, can be obtained both at a high synthesis ratio and in an economically advantageously manner. We have now completed the present invention based on this finding.

More specifically, the present invention relates to a process for the-preparation of a polyol fatty acid ester having a mixed acid residue, which comprises reacting a partial ester of a polyol having a branched fatty acid with a straight-chain fatty acid or a lower alcohol ester thereof in the presence of a lipase. The object of the present invention is to provide a process in which a polyol ester having a mixed acid residue of a branched fatty acid and a straight-chain fatty acid in the molecule can be easily obtained at a high concentration as not attainable by conventional chemical process.

The process for preparing a polyol ester having a mixed acid residue of a branched fatty acid and a straight-chain fatty acid in the molecule according to the present invention is characterized in that a partial ester of a polyol having a branched fatty acid is reacted with a straight-chain fatty acid or a lower alcohol ester thereof in the presence of a lipase. Namely, the fact that the reactivity of a lipase with a branched fatty acid is very low is utilized. More specifically, the polyol partial ester having a branched fatty acid is neither hydrolyzed nor transesterified in the presence of a lipase, but only the straight-chain fatty acid or its ester is esterified or alcoholyzed. Accordingly, the straight-chain fatty acid is selectively esterified with the remaining hydroxyl group of the partial ester of the polyol with the branched fatty acid as the starting material, whereby a product having a high purity can be obtained in a high yield. As is seen from the foregoing description, the invention has been completed by utilizing the characteristics of the lipase effectively.

In the invention, a polyol fatty acid ester having mixed acid groups is produced by reacting a partial ester of a polyol and a branched fatty acid with a straight-chain fatty acid or a lower alcohol ester thereof in the presence of a lipase. The obtained glyceride mixture contains a large amount of a diglyceride, or a di-acylglycerol, having a branched, saturated fatty acid group or residue and a straight-chain fatty acid residue or group, saturated or unsaturated.

The esterification reaction may be conducted while water is being removed. It is preferable that the lipase used here is one which reacts with the polyol selectively at the alpha-position of the polyol. Polyols include alkane diols and alkane triols.

It is preferred that the partial ester has a branched fatty acid residue which is saturated and having 7 to 24 carbon atoms and said straight-chain fatty acid has 8 to 22 carbon atoms.

The invention moreover provides a glyceride mixture obtained by the process as above. It contains 60 to 100 wt. %, especially 60 to 97 wt. %, of a diglyceride or di-acylglycerol having one branched acyl group and one straight-chain acyl group.

The di-acylglycerol obtained in the invention is defined with the formula (I):

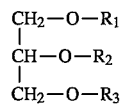

in which one of R1, R2 and R3 is a straight-chain fatty acid residue, saturated or unsaturated, having 8 to 22 carbon atoms, another is a branched, saturated fatty acid residue having 7 to 24 carbon atoms and the other is hydrogen.

It is preferable that one of R1, R2 and R3 is a straight-chain fatty acid group having 18 to 22 carbon atoms, another is a 2-ethylhexanic acid group and the other is hydrogen.

It is also preferable that one of R1, R2 and R3 is a branched, saturated fatty acid group selected from the group consisting of:

(a) methyl-isostearic acid group having the formula:

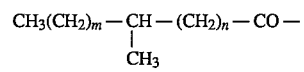

in which m and n each are an integer of 4 to 10, the sum total of m and n is 14 and m and n each have a distribution with a center of 7, (b) 5,7,7-trimethyl-2-(1,3,3-trimethylbutyl)-octanoic acid group and (c) 2-heptylundecanoic acid group, another is a teteradecanoic acid group and the other is hydrogen.

The invention, in addition, provides a glyceride mixture which comprises zero to 40 percent by weight of monoglyceride, 60 to 100 percent by weight of di-acylglycerol and zero to 20 percent by weight of triglyceride, the acyl group of the glycerides being selected from (i) a straight-chain fatty acid residue having 8 to 22 carbon atoms and (ii) a branched, saturated fatty acid residue having 7 to 24 carbon atoms, with the diglyceride comprising 60 to 100 percent by weight of the di-acylglycerol having both groups (i) and (ii), zero to 40 percent by weight of the di-acylglycerol having two groups (i) and zero to 40 percent by weight of the di-acylglycerol having two groups (ii).

The invention provides an external preparation which comprises the glyceride mixture as defined above and a cosmetic component for the skin or hair, a medical drug, a cosmetic composition which comprises the glyceride mixture and a cosmetic component and an oily composition containing the glyceride mixture.

DETAILED DESCRIPTION OF THE INVENTION

The present invention will now be described in detail.

As the polyol used in the present invention, there can be mentioned alkanediols such as ethylene glycol, propylene glycol (1,2-propanediol), 1,3-propanediol, 1,2-butanediol, 1,3-butanediol, 1,4-butanediol, 2,3-butanediol, 1,5-pentanediol, 2,4-pentanediol, 1,6-hexanediol, 2,5-hexanediol, 1,8-octanediol and 2,7-octanediol, alkanetriols such as 1,2,4-butanetriol, glycerol and 1,2,6-hexanetriol, and dimers, trimers and polymers thereof represented by diglycerol.

As the branched fatty acid and straight-chain fatty acid used in the present invention, there can be mentioned saturated and unsaturated fatty acids having 4 to 24 carbon atoms. As the branched fatty acid, there can be mentioned, for example, trialkyl-acetic acids, 2-alkyl-branched acids, methyl-branched acids and polybranched acids. More specifically, there can be mentioned 2-ethylhexanoic acid, isopelargonic acid, isomyristic acid and isostearic acid. As the straight-chain fatty acid, there can be mentioned valeric acid, caproic acid, enanthoic acid, caprylic acid, pelargonic acid, capric acid, lauric acid, myristic acid, palmitic acid, stearic acid, arechic acid, behenic acid, lignoceric acid, palmitoleic acid, oleic acid, elaidic acid, erucic acid, sorbic acid and linoleic acid. These straight-chain fatty acids may be in the form of esters with a lower alcohol having 1 to 3 carbon atoms, such as methanol, ethanol or propanol. In the present invention, the above-mentioned branched fatty acids, straight-chain fatty acids and alcohol esters thereof can be used, but the fatty acids and lower alcohol esters are not particularly critical.

Any lipase capable of synthesizing esters can be arbitrarily used for carrying out the present invention. For example, there can be mentioned lipases derived from microorganisms belonging to the genera Rhizopus, Aspergillus, Mucor, Geotrichum, Pseudomonas, Penicillium, Chromobacterium, Candida, Achromobacter and Alcaligenes. Of these lipases, those capable of acting selectively on the α-position of the polyol are especially preferred because especially valuable intended compounds are produced. For example, in the case where a glycerol fatty acid ester (diglyceride) containing 1 mole each of a branched fatty acid and a straight-chain fatty acid is synthesized, a monoester of glycerol with the branched fatty acid can be reacted with the straight-chain fatty acid in the presence of a lipase selective to the α-position. The stable type of a monoester of glycerol with a branched fatty acid ester is an α-monoglyceride, and by the action of a lipase selective to the α-position on the other α'-position, a diglyceride containing both a branched fatty acid and straight-chain fatty acid, which has a very high purity, can be easily obtained. As the lipase selective to the α-position, which is effective for the production of a diglyceride containing both of a branched fatty acid and a straight-chain fatty acid, there can be mentioned, for example, *Rhizopus delemer, Rhizopus japonicus, Mucor miehei* and *Muco javanicus*.

A crude enzyme obtained by isolation and purification can be directly used as the lipase, but from the economcial viewpoint, it is preferred that the lipase be used in the form of a so-called lipase preparation (immobilized lipase) obtained by immobilizing a lipase on a carrier.

A process in which a reaction mixture containing a partial ester of a polyol with a branched fatty acid and a straight-chain fatty acid or its lower alcohol ester as the substrate, in which a lipase is present, is dehydrated in the presence or absence of an organic solvent (exclusive of a primary alcohol solvent) without substantial addition of water, is especially effective.

An optimum reaction temperature should be selected according to the intended product and the fatty acids as the starting substrate. It is preferred that the reaction be carried out at a temperature of from 10 to 90° C. If the reaction temperature is lower than 10° C., the reaction mixture tends to become heterogeneous, and if the reaction temperature is higher than 90° C., the activity of the lipase is reduced.

According to the present invention, a polyol ester containing a branched fatty acid and a straight-chain fatty acid in the molecule, which has a high purity, can be obtained in a high yield. This mixed acid-polyol ester has characteristic properties. Therefore, the process of the present invention can be widely applied to the production of cosmetics, perfumes, medicines and chemical products such as lubricants and additives to plastics.

The glyceride mixture of the invention is useful in combination with other components to obtain a composition such as an external preparation, liquid oil and solid cosmetics. The invention is shown below in this respect.

EXTERNAL PREPARATION

The amount of the diacylglycerin to be added to the external preparation according to the present invention is generally 0.1 to 90% by weight, preferably 0.1 to 50% by weight, although it may widely vary depending upon the form of the preparation.

The other raw materials, except water, to be used in the present invention include nearly all materials which are ordinarily applied to external preparations, for examples, oils, surfactants, humectants including polyhydric alcohols, various drugs, preservatives and perfumes, and may be suitably selected from among these components depending upon the object, field of application and form of the preparation. For example, the oils include solid fats such as stearic and myristic acids, cetanol, stearyl alcohol, cholesterol and vaseline and liquid oils such as squalane, cholesteryl isostearate, jojoba oil, olive oil, neopentyl glycol dicaprate and liquid paraffin. The polyhydric alcohols include glycerin, 1,3-butylene glycol, propylene glycol, dipropylene glycol and polyethylene glycol. The surfactants include polyoxyethylene hardened castor oil, sorbitan fatty acid esters, polyoxyethylene sorbitan fatty acid esters, polyethylene glycol fatty acid esters, alkyl glyceryl ethers, fatty acid salts and alkyl phosphates.

The external preparations according to the present invention include ointments, creams, milky lotions and lotions.

| Component | Form of preparation (wt. %) | | | |
|---|---|---|---|---|
| | Ointment | Cream | Milky lotion | Lotion |
| oil | 0~70 | 0~50 | 0~20 | 0~5.0 |
| the diacylglycerin of the present invention | 1~50 | 0.5~30 | 0.5~10 | 0.1~5.0 |
| surfactant | 0~5.0 | 0.5~5.0 | 0.5~3.0 | 0.1~2.0 |
| polyhydric alcohol | 0~30 | 0~20 | 0~10 | 0~40 |
| water | 0~20 | 10~70 | 30~80 | 50~90 |

The diacylglycerin represented by the general formula (I) to be used in the present invention is one which is liquid at room temperature, exhibits high resistance to oxidation and decomposition, has low irritation and imparts an agreeable touch to the skin or hair. Namely, although a diacylglycerin having residues of an unsaturated fatty acid such as oleic acid or a short-chain fatty acid such as octanoic acid is also a liquid, a diacylglycerin having residues only of an unsaturated fatty acid is problematic in its resistance to oxidation, while one having residues only of a short-chain fatty acid is problematic in irritativeness. In contrast to these diacylglycerins, the diacylglycerin of the present invention having, in its molecule, both a $C_{18}$ branched fatty acid residue and a tetradecanoic acid residue is not problematic in these regards.

The external preparation containing the diacylglycerin as described above well suits the owing to the absence of a crystalline substance therein and is excellent in the persistency of its humectant effect for skin.

LIQUID OIL

The prepared diacylglycerin having a branched saturated fatty acid residue and a myristic acid residue according to the present invention has the following characteristics: (1) it is a liquid at ordinary temperatures, (2) it is chemically stable owing to its saturated hydrocarbyl group, (3) the decomposition of the myristoyl ester group is remarkably slight and (4) it is very agreeable to the touch of skin. Therefore, the diacylglycerin is particularly useful as a liquid oil for cosmetics or external preparations which are applied directly to the skin. A component which is crystalline at ordinary temperatures is inconvenient for handling, because it must be molten by heating prior to its use. Further, when such a component is contained in an emulsion system, it crystallizes with time to finally cause phase separation. The diacylglycerin having a branched saturated acid residue and a myristic acid residue according to the present invention is liquid at ordinary temperatures and exhibits, as a polar oil, a characteristic of stabilizing an emulsion system. The diacylglycerin according to the present invention may be used alone as a liquid oil for cosmetics or drugs or as a mixture with conventional oil, vaseline, liquid paraffin or natural fat.

SOLID COSMETIC

The glyceride mixture thus obtained is decolored and deodorized by ordinary methods to give a colorless and odorless mixture mainly comprising the diglyceride of the present invention, which is not an irritant to the skin and exhibits excellent amorphous properties including good spreadability. This mixture has excellent characteristics favorable for use as a solid oily base for cosmetics and drugs.

When the fatty acid diglyceride according to the present invention is prepared by a process as described above, it is generally obtained as a mixture of various glycerides. The content of the diglyceride represented by the general formula (I) in the mixture is at least 40% (by weight, the same applies hereinafter), preferably at least 50%. If the content is less than 40%, the glyceride mixture will be poor in spreadability and touch. Further, it is necessary that the content of a diglyceride having two residues of a straight-chain saturated fatty acid having 18 to 22 carbon atoms in the mixture does not exceed 20%, while that of a diglyceride having two 2-ethylhexanoic acid residues therein does not exceed 10%. If either of the contents exceeds its upper limit as described above, its spreadability will be low.

In the preparation of the fatty acid diglyceride according to the present invention, mono- and tri- glycerides are also generated in addition to the above diglyceride. It is preferred that these mono- and tri-glycerides be removed by purification as completely as possible. Particularly, a monoglyceride exerts an adverse effect on the excellent spreadability and touch resulting from the diglyceride, so that the content thereof must not exceed 20%, preferably 10% On the other hand, a triglyceride gives a heavy feeling, as the content thereof increases, though it exerts less influence upon the spreadability. Therefore, it is necessary that the content thereof must not exceed 40%.

Further, the glyceride mixture containing the diglyceride represented by the general formula (I) according to the present invention has preferably a solid fat content at ordinary temperatures (0° to 35° C.) (as determined by the NMR method based on the temporary solid fat content; established by the Japan Oil Chemists' Society) of at least 50%.

The solid cosmetic of the present invention mainly comprises an oily component for cosmetics and a pigment component for cosmetics. The oily component for cosmetics to be used in the present invention includes not only fatty acid diglycerides represented by the general formula (I) but also any other solid and liquid oily substances which are usable for cosmetics and mixtures thereof. Examples of the solid or semi-solid oily substance include carnauba wax, candelilla wax, rice wax, Japan wax, beeswax, ceresin wax, microcrystalline wax, paraffin wax, polyethylene wax, hardened beef tallow, hardened castor oil, hardened jojoba oil, lanolin and vaseline.

Examples of the liquid oily substance include hydrocarbons such as liquid paraffin, liquid isoparaffin (liquid polyisobutylene) and squalane; natural animal and vegetable oils such as olive oil, castor oil and jojoba oil; silicone oils such as dimethylpolysiloxane and synthetic ester oils such as isopropyl myristate.

The pigment for cosmetics to be used in the present invention includes all known pigments which are usable for cosmetics and mixtures thereof. Particular examples thereof include extender pigments such as talc, sericite, mica, kaolin, silica, nylon powder, polyethylene powder, silk powder and cellulose powder; coloring agents such as carbon black, titanium oxide, iron oxides, zinc oxide, ultramarine blue, iron blue, chromium oxide, organic tar dyestuffs and lakes and composite pigments such as micaceous titanium and iron oxide-coated mica. Further, examples thereof include pigments obtained by coating the above pigments with silicone, higher fatty acids, higher alcohols, fatty acid esters, metal soaps, amino acids or alkyl phosphates.

The contents of the oily component for cosmetics and the pigment component for cosmetic in the solid cosmetic according to the present invention are preferably 4 to 100% by weight and 0 to 96% by weight respectively, while the ratio of the fatty acid diglyceride represented by the general formula (I) based on the oily component is preferably 0.5 to 80% by weight, more preferably 1 to 50% by weight and most preferably 2 to 40% by weight, though it varies depending upon the form of the cosmetic. It is preferred that the content of the fatty acid diglyceride be relatively high for a system containing a liquid oil in a high ratio, while the content be relatively low for a system containing a solid fat in a high ratio and a liquid oil in a low ratio. When the ratio of the fatty acid diglyceride is less that 0.5% by weight, the effect will be poor, while when it exceeds 80% by weight, no additional effect will be attained, which is uneconomical.

Further, the solid cosmetic of the present invention may, if necessary, contain other conventional components for cosmetics. Examples of such components include other oily components, surfactants, drugs, preservatives, antioxidants and perfumes.

BRIEF DESCRIPTION OF DRAWING

FIG. 1 is a graph showing the relationship between the temperature and break strength with respect to the lip creams A and B prepared in Composition Example 6.

EXAMPLE 1

A four-neck flask having a capacity of 5 l was charged with 1000 g of isostearin monoglyceride or isostearoyl glycerol [2.79 moles, isostearic acid used is 5,7,7-trimethyl-2-(1,3,3-trimethylbutyl) octanoic acid supplied by Nissan Kagaku], 640 g (2.81 moles) of myristic acid and 150 g of Olipase (2800 U/g; supplied by Amano Seiyaku), and reaction was carried out at 50° C. under 100 Torr for 5 hours with stirring to prepare isostearomyristin diglyceride. In the obtained reaction product, the ester synthesis ratio was 90%. The ester synthesis ratio referred to herein is the ratio, expressed in terms of %, of the amount of the fatty acid consumed for esterification to the amount of the fatty acid as the substrate in the charged reaction mixture. The reaction product was passed through a thin-film evaporator at 190° C. under 0.03 Torr to remove unreacted isostearin monoglyceride and myristic acid and obtain 1310 g of intended isostearomyristin diglyceride as the distillation residue.

The composition of the product was analyzed by gas chromatography (GLC) using a fused silica capillary (DB-1 supplied by J & W). It was found that the product comprised 3% of a monoglyceride, 89% of a diglyceride and 8% of a triglyceride and the diglyceride comprised 9% of diisostearin glyceride, 91% of isostearomyristin diglyceride and 0% of dimyristin glyceride.

EXAMPLE 2

A four-neck flask having a capacity of 5 l was charged with 1000 g (4.59 moles) of 2-ethylhexane monoglyceride, 1500 g (4.41 moles) of behenic acid and 200 g of a commercially available lipase preparation, Lipozyme 3A (lipase derived from *Mucor miehei*, immobilized on an anion-exchange resin; supplied by Novo Industri A.S.), and reaction was carried out at 75° C., under 220 Torr for 3 hours with stirring. The reaction product obtained at an ester synthesis ratio of 96% was passed through a thin-film evaporator at 185° C. under 0.05 Torr to obtain 2210 g of 2-ethylhexanobehenin diglyceride as the distillation residue.

When the product was analyzed according to the GLC method described in Example 1, it was found that the product comprised 0% of a monoglyceride, 88% of a diglyceride and 12% of a triglyceride and the diglyceride comprised 0% of di-2-ethylhexane glyceride, 91% of 2-ethylhexanobehenin diglyceride or 2-ethylhexanoylbehenoyl glycerol and 9% of dibehenoyl glycerol.

EXAMPLE 3

A four-neck flask having a capacity of 5 l was charged with 1000 g of a monoester of trimethylene glycol with isomyristic acid (3.50 moles; monoester synthesized by using isomyristic acid supplied by Nissan Kagaku), 1100 g (3.24 moels) of behenic acid and 200 g of Lipozyme 3A used in Example 2, and 2000 ml of hexane was further added to dissolve behenic acid. A tube for separating and refluxing hexane and water was set to the flask and reaction was carried out at 55° C. with stirring under reduced pressure for 6 hours. The lipase preparation was removed by filtration. In the obtained reaction product, the ester synthesis ratio was 83%. In the same manner as described in the foregoing examples, the reaction product was passed through a thin-film evaporator at 200° C. under 0.05 Torr to give 1730 g of an intended isomyristobehenic diester of triethylene glycol as the distillation residue.

By the GLC analysis of the obtained product, it was found that the product comprised 100% of a diester of trimethylene glycol and the diester comprised 2% of diisomyristic ester, 94% of isomyristobehenic ester or 1-isomyristoyl 3-behenoyl propanediol and 4% of dibehenate.

EXAMPLE 4

A three-necked flask of 500 ml was charged with 92 g (1 mol) of glycerine and 144.2 g (1 mol) of 2-ethyl hexanate and then 0.5 g of potassium hydroxide and 1.0 g of activated carbon. This reaction mixture was heated up to 150° C. to 260° C. for 2 to 4 hours to effect esterification. The product mixture was found, by way of gas chromatography, to comprise 0.9% of the fatty acid, 24.6% of glycerine, 46.4% of monoglyceride, 23.2% of diglyceride and 5.0% of triglyceride. The analysis by the gas chromatography was conducted at an injection temperature of 350° C., determination temperature of 345° C., with a column of DB-1, at a column temperature of 100° C. up to 340° C., at a flow rate of 10° C. per minute.

The product mixture was neutralized with 85% phosphoric acid solution and it was heated at 150° to 240° C. for 1 to 3 hours in nitrogen gas to top the unreacted glycerine and fatty acid. The activated carbon was removed out with filtration. Then molecular distillation was carried out to distil out the monoglyceride. The obtained composition was found to comprise a trace amount of the fatty acid, a trace amount of glycerine, 87.0% of monoglyceride, 13.0% of diglyceride and a trace amount of triglyceride.

Then another three-necked flask of 500 ml was charged with 73 g (0.281 mol) of the composition and 95.6 g (0.281 mol) of behenic acid and then 25.3 g (15%) of an enzyme to react selectively at a specified position. The reaction mixture was heated at 65° to 90° C. for 1 to 5 hours at a reduced pressure to effect a reaction. After the reaction, the enzyme was filtrated out and then the unreacted monoglyceride and behenic acid were distilled out. The obtained product mixture was found to comprise a trace amount of 2-ethylhexyl monoglyceride, a trace amount of behenic acid, 75.8% of beheno(C22)-2-ethylhexyl diglyceride or 2-ethylhexanolbehenoyl-glycerol, 1.2 g of other diacylglycerols and 23.0% of triacylglycerol.

EXAMPLE 5

A three-necked flask of 500 ml was charged with 92 g (1 mol) of glycerine and 284.3 g (1 mol) of isostearic acid and then 0.75 g of potassium hydroxide and 1.5 g of activated carbon. This reaction mixture was heated up to 150° to 260° C. for 4 to 16 hours to effect esterification. The product mixture was found, by way of gas chromatography having the same conditions as shown in Example 4, to comprise 1.6% of the fatty acid, 6.7% of glycerine, 48.3% of monoglyceride, 31.3% of diglyceride and 10.0% of triglyceride.

The product mixture was neutralized with 85% phosphoric acid solution and then heated at 150° to 240° C. for 1 to 3 hours in nitrogen gas to top the unreacted glycerine. The activated carbon was filtrated out. Molecular distillation was effected to distil out the fatty acid. Then the monoglyceride was distilled out. The obtained composition was found to comprise 2.8% of the fatty acid, a trace amount of glycerine, 95.5% of monoglyceride, 1.6% of diglyceride and 0.1% of triglyceride.

Another three-necked flask of 500 ml was charged with 107.4 g (0.3 mol) of the composition and 102 g (0.3 mol) of behenic acid and then 31.4 g of an enzyme. The reaction mixture was heated at 60° to 90° C. for 1 to 10 hours at a reduced pressure. After the reaction, the enzyme was filtrated out and the unreacted monoglyceride and behenic acid were distilled out. The obtained glyceride mixture was found to comprise a trace amount of isostearin monoglyceride, a trace amount of behenic acid, 83.2% of beheno(C22)-isostearin diglyceride or behenoyl-isostearoyl-glycerol, 1.2% of other di-acylglycerols and 15.6% of triacylglycerol.

EXAMPLE 6

A branched fatty acid monoglyceride and a straight fatty acid, as listed below, were reacted with each other in the same manner as shown in Example 2. Each obtained product mixture was shown below in view of its composition and viscosity at 25° C. All the products were found not to be irritant to human eyes and skin. In the starting monoglycerides, isoheptyl monoglyceride, isononan monoglyceride and isomyristin monoglyceride were produced from propylene and butene by way of polymerization and aldol condensation. They had two or three branched methyls, being available from Nissan Chemical Co., Ltd. in the tradename of Fine Oxocol.

| starting material branched fatty acid of monoglyceride | straight fatty acid | composition of glycerides (wt. %) | | | viscosity (cps) |
|---|---|---|---|---|---|
| | | mono- | di- | tri- | |
| isoheptyl acid | myristinic acid | 4 | 82 | 14 | 54 |
| 2-ethylhexanic acid | myristinic acid | 0 | 95 | 5 | 50 |
| isononanic acid | myristinic acid | 0 | 73 | 27 | 76 |
| isomyristinic acid | myristinic acid | 0 | 79 | 21 | 104 |

Reference Example 1

568 g (2.0 mol) of isostearic acid [5,7,7-trimethyl- 2-(1, 3,3-trimethylbutyl)octanoic acid; a product of Nissan Chemical Industries, Ltd.] was fed into a 2-l reactor fitted with a thermometer, a reflux condenser, a dropping funnel and a stirrer. 286 g (2.4 mol) of thionyl chloride was dropwise added to the reactor through the dropping funnel under stirring, while passing nitrogen gas therethrough. As the dropwise addition of thionyl chloride proceeded, the color of the mixture turned from colorless into pale yellow and dark brown successively, with the generation of gas. During the dropwise addition, the reaction mixture was kept at a room temperature. After about 3 hours, the dropwise addition of thionyl chloride was completed. Then, the reaction mixture was kept at a temperature of 60° to 70° C. in an oil bath for about 3 hours. It was confirmed that the generation of gas nearly discontinued. The reaction mixture was distilled under a reduced pressure to remove low-boiling substances, followed by steam distillation. 588 g of a cut of 112° to 120° C./0.1 to 0.3 mmHg was recovered (yield: 97 %). This cut was identified with 5,7,7-trimethyl-2-(1,3,3-trimethylbutyl)octanoyl chloride.

IR spectrum (liquid film method) 2970, 2920, 2875, 1795 (C=O stretching), 1480, 1390, 1370, 1260, 1210, 995, 930, 790, 710, 600 cm$^{-1}$ H$^1$-NMR spectrum (CCl$_4$ solvent): δ

0.9 (s, 24H, C$\underline{H}_3$—)

1.1~2.0 (m, 10H, —C$\underline{H}_2$— and —$\overset{|}{\underset{|}{C}}$—H)

2.5 (m, 1H, 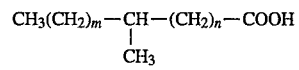CHCOCl)

REFERENCE EXAMPLE 2

568 g (2.0 mol) of isostearic acid (a methyl-branched fatty acid represented by the following formula; Emery 875 isostearic acid of Emery, U.S.A.) was reacted with 520 g (4.4 mol) of thionyl chloride in a 3-l reactor fitted with the same devices as those used in Reference Example 1.

$$CH_3(CH_2)_m-\underset{\underset{CH_3}{|}}{CH}-(CH_2)_n-COOH$$

wherein m and n are each an integer of 4 to 10 with the proviso that the sum total of m and n is 14 and that both are distributed with a point of m=n=7 as the center.

After the completion of the reaction, the reaction mixture was distilled under a reduced pressure to recover about 230 g of a low-boiling substance which was thought to be thionyl chloride. Then, the residue was further distilled under a reduced pressure to obtain 454 g of a cut of 153° to 170° C./1.0 to 3.0 mmHg (yield: 75 %). This cut was identified with methyl-branched isostearoyl chloride.

IR spectrum (liquid film method) 2950, 2920, 2550, 1800 (C=O stretching), 1460, 1400, 1380, 950, 720, 680, 590 cm$^{-1}$ H$^1$-NMR spectrum (CCl$_4$ solvent): δ

0.6~1.0 (m, CH$_3$CH$_2$— and —C$\underline{H}$—)
$\qquad\qquad\qquad\qquad\qquad\qquad\quad |$
$\qquad\qquad\qquad\qquad\qquad\qquad\;\, CH_3$ 1.0~1.5 (m, —C$\underline{H}_2$—)

1.5~2.0 (m, —C$\underline{H}$—)
$\qquad\qquad\;\, |$
$\qquad\qquad\; CH_3$ 2.77 (t, C$\underline{H}_2$COCl)

REFERENCE EXAMPLE 3

568 g (2.0 mol) of 2-heptylundecanoic acid, 184 g (2.0 mol) of purified glycerin and 1.2 g of potassium hydroxide were fed into a 2-l reactor fitted with a thermometer, a nitrogen capillary, a reflux condenser (provided with a water separator) and a stirrer to carry out the esterification at 230° to 240° C., while passing nitrogen gas therethrough. After about 10 hours, it was confirmed that the generation of water nearly discontinued. The reaction mixture was distilled under a reduced pressure to remove unreacted glycerin under the conditions of 210° to 220° C./15 to 25 mmHg. After the removal of the glycerin had been nearly completed, the reaction mixture was distilled with a molecular distillation still of a thin film type to obtain 246 g of a cut of 170° to 175° C./0.03 to 0.05 mmHg. This cut was identified with mono-2-heptylundecanoylglycerin.

IR spectrum (liquid film method) 3440 (OH stretching), 2960, 2910, 2860, 1740 (C=O stretching), 1470, 1370, 1160, 740 cm$^{-1}$ H¹-NMR spectrum (CCl₄ solvent): δ

0.9 (t, 6H, C$\underline{H}_3$—)

1.1~1.6 (m, 28H, —C$\underline{H}_2$—)

2.3 (m, 1H, 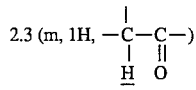)

2.7 (s, 2H, —O—$\underline{H}$)

3.5~4.2 (m, 5H, —C$\underline{H}_2$—O— and 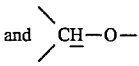)

Hydroxyl number: 311.8 (calculated: 312.9)

REFERENCE EXAMPLE 4

458 g (2.0 mol) of myristic acid, 184 g (2.0 mol) of purified glycerin and 0.9 g of potassium hydroxide were fed into a 2-l reactor fitted with the same device as used in Reference Example 3 to carry out the esterification at 230° to 240° C. for about 8 hours, while passing nitrogen gas therethrough. The reaction mixture was distilled under a reduced pressure to remove unreacted glycerin under the conditions of 210° to 220° C. and 15 to 25 mmHg. After the removal of the glycerin had been nearly completed, the reaction mixture was distilled in a molecular distillation still of a thin film type to obtain 230 g of a cut of 195° to 200° C./0.03 to 0.05 mmHg. This cut was identified with monomyristoylglycerin.

Hydroxyl number: 370.3 (calculated: 371.0)

EXAMPLE 7

303 g (1 mol) of monomyristoylglycerin, 1000 ml of benzene and 87 g (1.1 mol) of pyridine were fed in this order into a 3-l reactor fitted with a thermometer, a dropping funnel, a reflux condenser and a stirrer. The contents were heated to 50° C. in an oil bath under stirring, while passing nitrogen gas therethrough. 291 g (0.96 mol) of the 5,7,7-trimethyl-2-(1,3,3-trimethylbutyl)-octanoyl chloride prepared in Reference Example 1 was dropwise added to the reactor through the dropping funnel over a period of about 3 hours, while keeping the reaction mixture at about 50° C. After the completion of the dropwise addition, the reaction mixture was heated to 60° to 80° C. and stirred for about 5 hours. The resulting mixture was filtered to remove a white precipitate of pyridine hydrochloride. The obtained filtrate was distilled in a vacuum to remove the solvent and heated to 190° to 200° C. under a reduced pressure of 0.5 to 0.7 mmHg for about 5 hours to remove the residual acyl chloride completely. The obtained product was a mixture comprising di- and triacylglycerins obtained by esterifying one molecule of monomyristoylglycerin with one or two molecules of 5,7,7-trimethyl-2-(1,3,3-trimethylbutyl)octanoic acid respectively and unreacted mono-myristoylglycerin.

This mixture was subjected to column chromatography using Wako gel B-10 (mfd. by Wako Junyaku Kogyo) and a hexane/diethyl ether (70:30) mixture to obtain 360 g of a diacylglycerin fraction. This diacylglycerin fraction was a transparent and colorless liquid and identified with a diacylglycerin having a 5,7,7-trimethyl-2-(1,3,3-trimethylbutyl)octanoic acid residue and a myristic acid residue.

IR spectrum (liquid film method) 3500 (OH stretching), 2960, 2930, 2850, 1740 (C=O stretching), 1465, 1365, 1160, 720 cm⁻¹

H¹-NMR spectrum (CCl₄ solvent): δ

0.9 (s, 27H, —C$\underline{H}_3$)

1.2~1.6 (m, 22H, —C$\underline{H}_2$— and 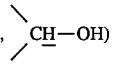)

2.3 (m, 3H, —C$\underline{H}$—CO—, —C$\underline{H}_2$—CO—)

2.9 (s, 1H, —O$\underline{H}$)

4.0~4.5 (m, 4H, —C$\underline{H}_2$—O—)

5.1 (m, 1H, \C$\underline{H}$—OH)

Acid value: 0.1 (calculated: 0) Hydroxyl number: 98.0 (calculated: 98.6)

EXAMPLE 8

303 g (1 mol) of the monomyristoylglycerin prepared in Reference Example 4, 1500 ml of benzene and 100 g (1.27 mol) of pyridine were fed in this order into a 3-l reactor fitted with the same devices as those used in Example 7. The contents were heated to 50° C. in an oil bath, while passing nitrogen gas therethrough. 291 g (0.96 mol) of the methyl-branched isostearoyl chloride prepared in Reference Example 2 was dropwise added to the reactor through the dropping funnel. After the completion of the dropwise addition, the contents were kept at 50° C. for about 3 hours and then at 70° to 80° C. for about 8 hours to thereby carry out the esterification completely. It was confirmed by IR spectroscopy that the reaction mixture did not contain any acyl chloride at all. The reaction mixture was treated in a similar manner to that used in Example 7 to obtain 372 g of a diacylglycerin having a methyl-branched isostearic acid residue and a myristic acid residue as a transparent and colorless liquid.

IR spectrum (liquid film method) 3480 (OH stretching), 2955, 2930, 2850, 1740 (C=O stretching), 1465, 1365, 1160, 720 cm⁻¹

H¹-NMR spectrum (CCl₄ solvent): δ

0.9 (m, 9H, —C$\underline{H}_3$)

1.2~1.6 (m, 49H, —C$\underline{H}_2$—, —C$\underline{H}$)

2.3 (m, 4H, —C$\underline{H}_2$—CO—)

2.9 (s, 1H, —O$\underline{H}$)

4.0~4.5 (m, 4H, —C$\underline{H}_2$—O—)

5.1 (m, 1H, 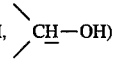)

Acid value: 0.1 (calculated: 0) Hydroxyl number: 97.4 (calculated: 98.6)

EXAMPLE 9

359 g (1 mol) of the mono-2-heptylundecanoylglycerin prepared in Reference Example 3, 274 g (1.2 mol) of myristic acid and 80 g of a commercially available lipase preparation Lipozyme 3A [lipase from Mucor miehei immobilized with an anion exchange resin; mfd. by Novo Industri, A.S.] were added to a 2-l reactor fitted with a thermometer, a reflux condenser and a stirrer. The contents were heated to 50° C. and stirred under a reduced pressure of 100 to 300 mmHg for 5 hours to carry out the esterification. After the completion of the reaction, the lipase preparation was filtered out and the filtrate was distilled in a molecular distillation still of a thin film type under the conditions of 190° to 195° C. and 0.03 to 0.05 mmHg to remove excess myristic acid and unreacted monoacylglycerin. Thus, 501 g of the objective diacylglycerin having a 2-heptylundecanoic acid residue and a myristic acid residue was obtained.

IR spectrum (liquid film method) 3480 (OH stretching), 2960, 2930, 2850, 1740 (C=O stretching), 1465, 1365, 1160, 720 cm$^{-1}$ $H^1$-NMR spectrum (CCl$_4$ solvent): δ

0.9 (m, 9H, —C$\underline{H}_3$)

1.2~1.6 (m, 50H, —C$\underline{H}_2$—)

2.3 (m, 3H, C$\underline{H}$—CO—, —C$\underline{H}_2$—CO—)

2.7 (s, 1H, —O$\underline{H}$)

4.0~4.5 (m, 4H, —C$\underline{H}_2$—O—)

5.1 (m, 1H, C$\underline{H}$—OH)

Acid value: 0.1 (calculated: 0) Hydroxyl number: 97.1 (calculated: 98.6)

Composition Example 1

A cream was prepared by homogeneously emulsifying a mixture having the following composition:

| (Component) | (Parts by weight) |
| --- | --- |
| stearic acid | 10.0 |
| cetyl alcohol | 5.0 |
| liquid paraffin | 2.0 |
| purified lanolin | 1.0 |
| glycerin | 5.0 |
| diacylglycerin* | 7.0 |
| methyl p-hydroxybenzoate | 0.2 |
| butyl p-hydroxybenzoate | 0.1 |
| purified water | 68.4 |
| perfume | 0.3 |

*The diacylglycerins prepared in Examples 7, 8 and 9 were used.

The obtained creams were subjected to the preservation test (state and odor) of 40° C. and 3 months and monitor test. In the monitor test, each cream was applied to the faces of 86 women of 20 to 40 years old which had been sampled at random to evaluate the feeling thereof in service according to the criteria which will be described.

The results are shown in Table 1.

<Evaluation criteria>

A very moist and agreeable to the touch

B indefinably agreeable to the touch

C lacking in particular characters

TABLE 1

| Example | Diacylglycerin | Preservation test 40° C./3 months | Monitor test A | B | C |
| --- | --- | --- | --- | --- | --- |
| Example 7 | 5,7,7-trimethyl-2-(1,3,3-trimethylbutyl)-octanoic acid/myristic acid | good | 79 | 7 | 0 |
| Example 8 | methyl-branched isostearic acid/myristic acid | good | 66 | 15 | 5 |
| Example 9 | 2-heptylundecanoic acid/myristic acid | good | 75 | 9 | 2 |

Composition Example 2 (Ointment)

| Oil phase components | |
| --- | --- |
| vaseline | 40% by weight |
| squalane | 10 |
| diacylglycerin prepared in Example 8 | 20 |
| POE(20) sorbitan monostearate | 3 |
| butylparaben | 0.1 |
| Aqueous phase components | |
| methylparaben | 0.2% by weight |
| glycerin | 10 |
| water | the balance |

An ointment was prepared from the above oil phase and aqueous phase components by the following process.

<preparation process>

Methylparaben and glycerin were added to water and the obtained mixture was kept at 70° C. Separately, the other lipophilic components were molten by heating to obtain a molten mixture of 70° C. This mixture was added to the above aqueous phase component mixture, followed by emulsification with an emulsifier. The obtained emulsion was cooled to a final temperature of 30° C. with a heat exchanger and charged to obtain an ointment according to the present invention.

The obtained ointment was an external preparation which exhibited a high affinity for the skin and was excellent in the persistency of its humectant effect for the skin.

Composition Example 3 (Cream)

| Oil phase components | |
| --- | --- |
| stearic acid | 2% by weight |
| cetanol | 1 |
| cholesterol | 1 |
| squalane | 10 |
| jojoba oil | 10 |
| diacylglycerin prepared in Example 7 | 10 |
| POE(40) hardened castor oil | 0.5 |
| cetyl phosphate | 0.5 |
| sorbitan monostearate | 2.0 |
| butylparaben | 0.1 |
| Aqueous phase components | |

Composition Example 3 (Cream) -continued

| | |
|---|---|
| methylparaben | 0.2% by weight |
| glycerin | 10 |
| 1,3-butylene glycol | 5 |
| perfume | 0.1 |
| potassium hydroxide | 0.1 |
| water | the balance |

A cream was prepared from the above oil phase and aqueous phase components by the following process.
<Preparation process>

The above aqueous phase components were mixed, melted by heating and kept at 70° C. Separately, the above oil phase components were mixed by heating to 70° C. to obtain a mixture. This mixture was added to the above aqueous phase component mixture, followed by emulsification with an emulsifier. The obtained emulsion was cooled to a final temperature of 30° C. with a heat exchanger and charged to obtain a cream according to the present invention.

The obtained cream was an external preparation which exhibited a high affinity for the skin and was excellent in its persistency of the humectant effect for the skin.

Composition Example 4 (milky lotion)

Oil phase components

| | |
|---|---|
| cetanol | 1% by weight |
| squalane | 5% by weight |
| olive oil | 3 |
| jojoba oil | 2 |
| diacylglycerin prepared in Example 9 | 5 |
| POE(10) hardened castor oil | 1 |
| sorbitan monostearate | 1 |
| butylparaben | 0.1 |

Aqueous phase components

| | |
|---|---|
| methylparaben | 0.1% by weight |
| glycerin | 2 |
| 1,3-butylene glycol | 2 |
| ethanol | 3 |
| perfume | 0.1 |
| water | the balance |

A milky lotion was prepared from the above oil phase and aqueous phase components in a similar manner to the one described in Composition Example 3.

The obtained milky lotion was an external preparation which exhibited a high affinity for the skin and was excellent in its persistency of the humectant effect for the skin.

Composition Example 5 (lotion)

Oil phase components

| | |
|---|---|
| diacylglycerin prepared in Example 8 | 2% by weight |
| POE(60) hardened castor oil | 1% by weight |

Aqueous phase components

| | |
|---|---|
| lactic acid | a suitable amount |
| sodium lactate | a suitable amount |
| glycerin | 3% by weight |
| 1,3-butylene glycol | 1.5 |
| polyethylene glycol 1500 | 0.5 |
| ethanol | 10 |
| perfume | 0.1 |
| water | the balance |

A lotion was prepared from the above oil phase and aqueous phase components by the following process.
<Preparation process>

Glycerin, 1,3-butylene glycol, polyethylene glycol 1500, lactic acid, sodium lactate and ethanol were dissolved in water to obtain a weakly acid aqueous solution (pH: 5 to 6). Separately, polyoxyethylene hardened castor oil, the diacylglycerin prepared in Example 5 and perfume were molten to obtain a molten mixture. This mixture was added to the above solution under stirring to obtain a lotion according to the present invention.

The obtained lotion was an external preparation which exhibited a high affinity for the skin and was excellent in its persistency of the humectant effect for the skin.

EXAMPLE 10 and 11

A mixture comprising 1 mol of glycerin, 1 mol of a fatty acid (a) given in Table 2, 1 mol of another fatty acid (b) given in Table 2 and 0.4% (based on the total feed) of active carbon was kept at a temperature of 150° to 260° C. to continue the reaction until the amount of the water generated by the esterification reached the theoretical value. After 2 to 4 hours, 90 to 100% based on the theoretical amount of water was liberated. Then, the reaction mixture was subjected to steam distillation at 150° to 200° C. for one hour to remove unreacted glycerin and fatty acids. The obtained residue was filtered to remove the active carbon. Thus, a glyceride mixture was obtained.

This glyceride mixture was chromatographed in a silica gel column to concentrate the diglyceride. The prepared diglyceride concentrate was subjected to solvent fractionation with five times by weight as much n-hexane as the concentrate to recover a medium-melting composition.

The components and their contents of the medium-melting composition finally obtained by the solvent fractionation are shown in Table 2.

TABLE 2

| | Fatty acid (a) | Fatty acid (b) | Glyceride composition[1] | | | Diglyceride composition[2] | | |
|---|---|---|---|---|---|---|---|---|
| | | | mono-glyceride | di-glyceride | tri-glyceride | high-melting diglyceride | medium-melting diglyceride | low-melting diglyceride |
| Ex. 10 | behenic acid | 2-ethyl-hexanoic acid | 0.5 | 99.0 | 0.5 | 2.9 | 94.1 | 2.0 |
| Ex. 11 | stearic acid | 2-ethyl-hexanoic acid | <0.1 | 99.0 | 1.0 | <0.1 | 94.7 | 4.3 |

Note) [1], [2] values (area ratios) as determined by gas chromatography
[2] The "high-melting diglyceride" refers to a diester with a fatty acid (a) and the "low-melting diglyceride" refers to a diester with a fatty acid (b), while the "medium-melting diglyceride" refers to a mixed acid diester with fatty acids (a) and (b).

Composition Example 6

(lip cream)

A mixture having a composition given in Table 3 was heated to 80° C., homogeneously kneaded, cast into a mold and cooled to prepare a solidified lip cream.

The lip creams A and B prepared were examined organoleptically for feeling in service by twenty nonexpert women. The results are shown in Table 4.

Further, the lip creams A and B were examined for break strength at various temperatures according to the method which will be described below. The results are shown in FIG. 1.

<Method for measurement of break strength>

Among the products (lip creams) shown in Table 3, the products A and B of the invention, molded into a cylinder having a diameter of 11 mm were stored at each temperature and examined for break strength by the use of a rheometer (NRM-20105 mfd. by Fudow Industrial Co., Ltd.). The examination was carried out by applying a stress at a distance of 10 mm from the fixed position at a speed of 10 mm/sec in the vertical direction to determine the maximum stress until the breaking of the stick. The maximum stress was regarded as break strength.

TABLE 3

| | Sample code Products of the present invention | |
|---|---|---|
| Composition | A | B |
| carnauba wax | 5 parts | 5 |
| ceresin | 10 | 10 |
| candelilla wax | 4 | 4 |
| beeswax | — | — |
| hardened coconut oil | — | — |
| diglyceride of Ex. 10 | 10 | — |
| diglyceride of Ex. 11 | — | 10 |
| lanolin | 12 | 12 |
| castor oil | 20 | 20 |
| olive oil | 39 | 39 |
| antioxidant | a suitable amount | ← |
| perfume | a suitable amount | ← |

TABLE 4

| | Formulation Products of the present invention | |
|---|---|---|
| Evaluation item | A | B |
| Spreadability | ⊙ | ○ |
| Unclamminess to the touch | ⊙ | ○ |

TABLE 4-continued

| | Formulation Products of the present invention | |
|---|---|---|
| Evaluation item | A | B |
| Unstickiness | ⊙ | ○ |

In Table 4,

⊙: The number of women who reported that the lip cream was excellent in each item is 16 or above.
○: The number of women who reported that the lip cream was excellent in each item is 12 to 15.

It can be understood from the results shown in Table 4 that the lip cream according to the present invention is excellent in spreadability, unclamminess to the touch and unstickiness.

Further, it can be understood from the results shown in FIG. 1 that the lip cream according to the invention exhibits little temperature dependence of break strength and exhibits an excellent feel in service over a wide temperature range. when the break strength is lower than 200 g, the resulting lip cream will be too soft to retain its shape, while when it is higher than 600 g, the lip cream will be so hard as to be disagreeable to the touch.

Composition Example 7

(lipstick)

Lipsticks having compositions given in Table 5 were prepared and examined for performance by ten expert panelists.

The results are shown in Table 6.

TABLE 5

| | Sample mark Products of the present invention | | | |
|---|---|---|---|---|
| Formulation | I | J | K | L |
| carnauba wax | 2 parts | 2 | 2 | 2 |
| ceresin | 4 | 4 | 4 | 4 |
| candelilla wax | 5 | 5 | 5 | 5 |
| microcrystalline wax | 2 | 2 | 2 | 2 |
| beeswax | 5 | 5 | 5 | 5 |
| lanolin | 4 | 4 | 4 | 4 |
| castor oil | 45 | 45 | 40 | 35 |
| hexadecyl alcohol | 24 | 20 | 20 | 15 |
| diglyceride of Ex. 10 | 1 | 5 | — | 10 |
| diglyceride | — | — | 10 | 10 |

TABLE 5-continued

| Formulation | Sample mark Products of the present invention | | | |
|---|---|---|---|---|
| | I | J | K | L |
| of Ex. 11 | | | | |
| titanium oxide | 2 | 2 | 2 | 2 |
| pigment (Red No. 202) | 2 | 2 | 2 | 2 |
| pigment (Red No. 204) | 1 | 1 | 1 | 1 |
| pigment (Yellow No. 4 A1-lake) | 3 | 3 | 3 | 3 |
| antioxidant | a suitable amount | ← | ← | ← |
| perfume | a suitable amount | ← | ← | ← |

TABLE 6

| Evaluation item | Sample code Products of the present invention | | | |
|---|---|---|---|---|
| | I | J | K | L |
| Spreadability | ○ | ⊙ | ⊙ | ⊙ |
| Unclamminess to the touch | ○ | ○ | ⊙ | ⊙ |
| Unstickiness | ○ | ⊙ | ⊙ | ⊙ |
| Independence of spreadability and touch on temperature | ○ | ○ | ⊙ | ⊙ |

(Note) Evaluation criteria
⊙: At least eight out of the ten panellists rated the product good.
○: At Least six out of the ten panellists rated the product good.

It can be understood from the above results that the lipstick according to the present invention is excellent in spreadability, unclamminess to the touch, unstickiness and independence of spreadability and touch on temperature.

Among the lip creams and lipsticks shown in Tables 3 and 5, the lip creams A and B and lipsticks J and K according to the present invention and the lip creams C and D and lipstick M for comparison were examined for sweating and blooming.

The sweating was evaluated by observing, with the naked eye, the sample which had been allowed to stand at 5° C. for 4 hours and then under the conditions of 35° C. and 60 RH for 4 hours, while the blooming was evaluated by observing, with the naked eye, the sample which had been allowed to stand at 35° C. for 8 hours and then at 5° C. for 24 hours.

Results are shown in Table 7, in which "-" indicates unobserved.

TABLE 7

| Sample | | Sample code | Sweating | Blooming |
|---|---|---|---|---|
| Lip cream | product of the present invention | A | — | — |
| | | B | — | — |
| Lipstick | product of the present invention | J | — | — |
| | | K | — | — |

Neither sweating nor blooming was observed in the products of the present invention. It can be understood from this fact that the quality of the product of the present invention is very stable.

Composition Example 8

(eyebrow pencil)

Eyebrow pencils having compositions given in Table 8 were prepared by the method which will be described below and evaluated for feel in service by ten expert panelists.

The results are shown in Table 9.

<Preparation method>

A mixture comprising the components was heated to 80° C., repeatedly kneaded with a roll mill, cooled to a room temperature and extruded through a nozzle with a press injection machine to obtain a core. This core was applied to wooden parts having a groove fit for the core, followed by bonding, combining and cutting. Thus, an eyebrow of a pencil type was obtained.

In a cosmetic of a pencil type, the hardness and softness of its core can be controlled by changing the ratio of the wax to the oil. However, the use of a low-melting wax generally gives a core which is soft and free from rough feelings, but is low in smoothness owing to its viscosity. Although the low smoothness is improved by using a saturated straight-chain fatty acid triglyceride having a sharp melting

TABLE 8

| Composition | Sample code Product of the present invention | |
|---|---|---|
| | N | O |
| Japan wax | 5 parts | 5 |
| hardened beef tallow | 5 | 5 |
| beeswax | 5 | 5 |
| diglyceride of Ex. 10 | 15 | — |
| diglyceride of Ex. 11 | — | 15 |
| paraffin | 5 | 5 |
| stearic acid | 15 | 15 |
| iron oxide black | 30 | 30 |
| iron oxide red | 10 | 10 |
| titanium oxide | 10 | 10 |

TABLE 9

| Evaluation criteria | Sample code Product of the present invention | |
|---|---|---|
| | N | O |
| Drawing easiness | 9 | 8 |
| Softness | 8 | 8 |
| Smoothness | 8 | 9 |

(Note) The figures in Table 9 each refer to the number of panelists who reported that the product was excellent as compared with the other.

point near body temperature, the improvement is insufficient.

It can be understood from the results shown in Table 9 that a cosmetic of a pencil type which has a soft feel and is excellent in smoothness can be obtained by using the diglyceride according to the present invention.

Composition Example 9

(compacted powder eye shadow)

Compacted powder eye shadows having compositions given in Table 10 were prepared by the method which will be described below and examined for physical properties and feelings in service.

The results are shown in Table 11.

<Preparation method>

The powder components were mixed in a blender by stirring to obtain a mixture. Separately, the oil components were homogeneously melted by heating and sprayed on to the mixture, followed by stirring. The resulting mixture was pulverized and press molded in a molding machine to obtain a compacted powder eye shadow.

TABLE 10

| Composition | Sample mark Product of the present invention | |
|---|---|---|
| | R | S |
| talc | 15 parts | 15 |
| sericite | 30 | 30 |
| micaceous titanium | 35 | 35 |
| ultramarine blue | 5 | 5 |
| iron oxide | 2 | 2 |
| squalane | 10 | 10 |
| lanolin | — | — |
| hardened palm oil | — | — |
| diglyceride of Ex. 10 | 2 | — |
| diglyceride of Ex. 11 | — | 2 |
| paraffin | 1 | 1 |

TABLE 11

| | Product of the present invention | |
|---|---|---|
| | R | S |
| Impact resistance*1 | O | O |
| Adherence to cosmetic chip*2 | O | O |
| Appearance (gloss)*3 | O | O |
| Adherence to the skin*3 | O | O |
| Gradatability*3 | O | O |

Note)
*1Evaluation of impact resistance
Ten compacted powder eye shadows, each placed in a dish-Like case made of aluminum, were made to fall from a height of 1 m onto an iron plate to observe whether fracture, crack or cutout was present or not.
O: Neither fracture nor crack nor cutout was observed in any of the ten eye shadows.
*2Evaluation of adherence to cosmetic chip
The surface of the eye shadow was rubbed with a cosmetic chip for eye shadow to determine the adherence of the eye shadow to the chip.
O: The eye shadow adhered uniformly.
*3Evaluation of appearance, adherence to the skin and gradatability
The appearance, adherence to the skin and gradatability in service were evaluated by ten expert panelists.
O: 7 or more out of the ten panelists rated the product good.

The appearance, adherence to the skin and gradatability in service were evaluated by ten expert panelists.
O: 7 or more out of the ten panelists rated the product good.

It can be understood from the results shown in Table 11 that the product containing the diglyceride according to the present invention exhibits excellent performances including high impact resistance, good adherence to the skin and gloss-free appearance.

Composition Example 10

(eye shadow of cream type)
Eye shadows of a cream type having compositions given in Table 12 were prepared by the method which will be described below and examined for feel in service by ten expert panelists.
The results are shown in Table 13.
<Preparation method>
The base materials were mixed and homogeneously melted by heating, followed by the addition of the pigments which had been previously mixed with each other. The obtained mixture was kneaded with a roll mill, molten again, deaerated, cast into a case and cooled being allowed to stand to obtain an eye shadow.
In Table 13,
⊚: 8 or more out of the ten panelists rated the product good.
it can be understood from the results that the product of the present invention is excellent not only in spreadability, spreading lightness and stickiness but also in gradatability.

TABLE 12

| Composition | Sample code Product of the present invention V |
|---|---|
| white petrolatum | 13 parts |
| acetylated lanolin | 5 |
| isopropyl lanolate | 2 |
| microcrystalline wax | 10 |
| liquid paraffin | 25 |
| diglyceride of Ex. 10 | 10 |
| titanium oxide | 10 |
| talc | 15 |
| ultramarine blue | 10 |
| preservative | a suitable amount |
| antioxidant | a suitable amount |

TABLE 13

| Evaluation | Sample code Product of the present invention V |
|---|---|
| Spreadability | ⊚ |
| Spreading lightness | ⊚ |
| Stickiness | ⊚ |
| Gradatability | ⊚ |

We claim:
1. A glyceride mixture comprising 60 to 100 wt. % of a diglyceride of the formula (I):

$$\begin{array}{l} CH_2-O-R_1 \\ | \\ CH-O-R_2 \\ | \\ CH_2-O-R_3 \end{array} \quad (I)$$

in which one of $R_1$, $R_2$ and $R_3$ is a branched fatty acid group selected from the group consisting of:
(a) methyl-isostearic acid group having the formula:

$$CH_3(CH_2)_m-\underset{\underset{CH_3}{|}}{CH}-(CH_2)_n-CO-$$

in which m and n each are an integer of 4 to 10, the sum total of m+n is 14 and m and n each have a distribution with a center of 7,
(b) 5,7,7-trimethyl-2-(1,3,3-trimethylbutyl)octanoic acid group and
(c) 2-heptylundecanoic acid group, another is tetradecanoic acid group and the other is hydrogen.

* * * * *